United States Patent [19]

Kovács et al.

[11] 4,368,333

[45] Jan. 11, 1983

[54] METHOD FOR THE CHEMICAL UTILIZATION OF COAL BY LIQUID PHASE OXIDATION

[75] Inventors: László Kovács; Galina Móger née Eremineva; Dezső Gál; Péter Hajdu; Julia Lukács; Erik Kroó; István Nemes; András Németh, all of Budapest; Katalin Szabó née Mogyorosi; Géza Szentgyörgyi, both of Tatabanya; Szilárd Riederauer, Budapest; János Szépvölgyi, Tatabanya, all of Hungary

[73] Assignee: Tatabányai Szénbányák, Tatabánya, Hungary

[21] Appl. No.: 288,761

[22] Filed: Jul. 31, 1981

[51] Int. Cl.³ .............................................. C07C 51/16
[52] U.S. Cl. .................................... 562/407; 562/408
[58] Field of Search ................................ 562/407, 408

[56] References Cited

FOREIGN PATENT DOCUMENTS 45-10723  4/1970  Japan ................................... 562/407

*Primary Examiner*—Alan Siegel
*Attorney, Agent, or Firm*—Karl F. Ross

[57] ABSTRACT

The invention relates to an improved method for the liquid phase oxidation of coal performed with oxygen optionally in the presence of water. According to the invention oxidation is performed in the presence of a cooxidation partner selected from the group of liquid hydrocarbons and oxygen-containing liquid hydrocarbons, and if water is also present, the pH of the homogeneous solution formed from the cooxidation partner and water is maintained at a slightly acidic value.

By the method of the invention the formation of carbon dioxide can be suppressed significantly.

5 Claims, No Drawings

METHOD FOR THE CHEMICAL UTILIZATION OF COAL BY LIQUID PHASE OXIDATION

The invention relates to an improved method for the chemical utilization of coal by subjecting it to oxidation in the liquid phase.

It is known that coal, either in naturally occurring or in pre-treated (e.g. coked) form, can be converted into oxidation products applicable in the chemical industry, such as alcohols, aldehydes, carboxylic acids, polycarboxylic acids, phenols, etc., by subjecting it to oxidation in the liquid phase. With respect to the nature of the oxidizing agent applied, the known methods of liquid phase oxidation can be divided into two main groups: i.e. methods utilizing oxygen and methods utilizing other oxidizing agents.

According to the methods belonging to the first group, coal is oxidized in an aqueous alkaline medium. The known methods differ from each other primarily in the parameters of the process (temperature, pressure, etc.). Thus e.g. according to the French Patent Specification No. 1,347,213 oxidation is performed at 260° C. under a pressure of 85 bars, to obtain 34.3% by weight of polycarboxylic acids, 6.75% by weight of oxalic acid and 53.7% by weight of carbon dioxide, all related to the carbon content of the starting coal.

In the methods belonging to the second group oxygen is replaced partly or completely by other oxidizing agents, such as hypochlorites or chlorine. Such processes are described, among others, in the German Patent Specifications Nos. 841,140, 864,992 and 879,103. In these methods water or an aqueous alkali is applied as the liquid phase. These methods yield primarily polycarboxylic acids as chemically useful substances, together with a considerable amount (about 20 to 60% by weight, related to the carbon content of the coal) of carbon dioxide.

Thus, the common disadvantage of all of the known methods is that a substantial part of the carbon content of the starting coal is converted into carbon dioxide, a substance which cannot be utilized chemically or thermally, considerably decreasing thereby the economy of the process. The formation of large amounts of carbon dioxide also involves that a significant amount of valuable energy source is lost in the oxidation process.

The invention aims at the elimination of the above disadvantages of the known methods.

It has been observed that when a cooxidation partner, in particular one or more liquid hydrocarbons, oxygen-containing liquid hydrocarbons or a mixture thereof, is added to the reaction mixture applied in the liquid phase oxidation of coal with oxygen, useless oxidation products (i.e. carbon dioxide and carbon monoxide) form only in very low amounts, generally 0.5 to 8% related to the carbon content of the coal converted, and the caloric value of the residual non-converted coal remains unchanged or even increases; thus a thermally well utilizable solid substance is obtained. These recognitions enable one to perform the liquid phase oxidation of coal more economically than before, with a particularly favorable energy balance.

Based on the above, the invention relates to an improved method for the liquid phase oxidation of coal with oxygen. According to the invention, oxidation is performed in the presence of one or more liquid hydrocarbons and/or oxygen-containing hydrocarbons.

Pure oxygen gas can also be applied as oxidizing agent in the method of the invention, from economical aspects it is, however, more advantageous to utilize oxygen-containing gas mixtures (such as air or air enriched with oxygen) for this purpose.

The term "liquid phase oxidation" means, in harmony with the terminology of the technical literature, that oxidation is performed in the presence of a liquid medium. The cooxidation partner applied may serve alone as the liquid medium, if desired, however, water can also be added to the system. When oxidation is performed in the presence of water, the pH of the aqueous medium should be maintained in the slightly acidic region, generally between about 5 and 6. The temperature and pressure conditions should be adjusted so that at least a part of the liquid substances introduced retain their liquid state during the whole process. Oxidation is performed generally at 160°–240° C. When air or air enriched with oxygen is applied as oxidizing agent, the partial pressure of oxygen may be adjusted e.g. to 0.6–2 MPa; this value corresponds to a total pressure of 3–6 MPa when air is applied.

Of the liquid hydrocarbons and oxygen-containing hydrocarbons usable as cooxidation partners according to the invention e.g. the following are to be mentioned: liquid aliphatic hydrocarbons, such as hexane, cyclohexane, nonane, decane, decaline and higher homologues thereof, liquid alkylaromatic hydrocarbons, such as tetraline, toluene, xylene, ethylbenzene and homologues thereof, liquid aromatic hydrocarbons, such as benzene and naphthalene, liquid hydrocarbon mixtures, such as petroleum, gasoline, Diesel-oil, etc., liquid aliphatic or aromatic ketones, such as methyl-ethylketone, acetone, cyclohexanone, acetophenone, benzophenone, etc., liquid aliphatic or aromatic alcohols, such as methanol, ethanol, butanol, isopropanol, cyclohexanol, benzyl alcohol, phenylethanol, etc., liquid ethers or cyclic ethers, such as dioxane, tetrahydrofuran, etc., liquid aliphatic or aromatic carboxylic acids, such as acetic acid, propionic acid, oleic acid, etc., and related compounds. The term "liquid" used in connection with the cooxidation partner means that the substance is liquid at room temperature.

According to a particularly preferred method liquid by-products or wastes obtained in the hydrocarbon industry are applied as cooxidation partners.

In the method of the invention generally 3 to 6 parts by weight of liquid medium are applied for one part by weight of coal. As already mentioned above, the liquid medium may consist of the liquid cooxidation partner only, or it may also contain water. The aqueous liquid media must be slightly acidic. Mineral acids or organic sulfonic acids can also be added to the liquid medium in order to ensure the slightly acidic character, it is more preferred, however, to adjust the pH of the mixture to the desired value (about 5–6) with organic carboxylic acids, which serve simultaneously as cooxidation partners. The ratio of water to the liquid cooxidation partner should be adjusted so that the liquid medium always remains a homogeneous solution. According to our observations neither emulsions nor multiphase liquid mixtures lead to the desired good results.

The weight ratio of coal to the liquid cooxidation partner may vary within wide ranges. If the liquid medium applied consists of liquid cooxidation partner only, the weight ratio may vary, as stated above, generally between 1:3 and 1:6. If, however, the liquid medium contains water as well, lower amounts of the cooxidation partner (e.g. 50 to 200 g, related to 1 kg of coal) are also sufficient to provide the desired result.

The presence of the liquid cooxidation partner in the liquid phase oxidation of coal involves the following advantages:

(1) The oxidation of carbon practically stops at the stage of carboxylic acid or polycarboxylic acid formation, i.e. industrially not utilizable products with higher oxidation degree (carbon dioxide and carbon monoxide) form only in insignificantly low amounts.

(2) The cooxidation partner participates in the oxidation process. Therefore, the composition of the product mixture can be influenced by the appropriate selection of the amount and quality of the cooxidation partner. Thus e.g. when acetophenone is applied as cooxidation partner, the proportion of benzoic acid increases in the reaction product, whereas when ethanol is the cooxidation partner, the product mixture contains aromatic oxy-compounds as major components. When by-products or wastes of the hydrocarbon industry are applied as cooxidation partners, these substances of less industrial value can also be converted into valuable chemical substances in the oxidation process.

(3) The excess of the cooxidation partner may also serve as an extraction medium for extracting certain components of the product mixture.

Apart from the appropriate selection of the quality and amount of the cooxidation partner, the composition of the product mixture can also be influenced upon modifying the reaction conditions or applying catalysts in the process. It has been observed that the share of polycarboxylic acids increases in the product mixture upon elevating the temperature or extending the reaction time. If the share of polycarboxylic acids is to be increased, salts containing $Co^{2+}$ and/or $Mn^{2+}$ cations and $Br^-$ anions or vanadium pentoxide may be added as catalysts to the reaction mixture. Vanadium pentoxide proved to be a particularly preferred catalyst.

The process of the invention is elucidated in detail by the aid of the following non-limiting Example.

EXAMPLE 50 g of A-0.1-0.2 grade coal mined at Felsőgalla (Hungary) were applied as the starting substance. The quality characteristics of the starting coal were as follows:

| carbon content | 65% by weight |
|---|---|
| humidity content | 11.1 " |
| sulfur content | 6.9 " |
| ash content | 17.9 " |
| caloric value | 20,600 kJ/kg |

This coal was oxidized under the following conditions:

| reaction time | 400 minutes |
|---|---|
| temperature | 190° C. |
| coal/liquid medium (weight ratio) | 1:6 |
| oxidizing agent | air |
| pressure | 6 MPa |
| partial pressure of oxygen | 0.7 MPa |
| rate of air supply | 2 dm$^3$/minute |

The quality and amount of the cooxidation partners applied in the individual tests, as well as the results obtained are summarized in the following Table.

| | Test 1 | Test 2 | Test 3 | Test 4 |
|---|---|---|---|---|
| Liquid medium (the cooxidation partner is underlined) | acetophenone | water/acetic acid/acetophenone 1:1:0.5 | water/acetic acid/acetophenone 1:1:0.5 | water/acetophenone 2.5:0.4 |
| Catalyst | — | — | 0.2 g of NaBr + 0.2 g of CoAc$_2$ | 0.3 g of V$_2$O$_5$ |
| Residual coal related to the amount of starting coal, % by weight | 85 | 50 | 50 | 50 |
| Sulfur content of the residual coal, % by weight | 6 | — | — | 3.4 |
| Water-soluble end-product* | 43.5 | 52 | 67 | 79 |
| Total amount of polyacids* | 14.5 | 13.3 | 18.1 | 26.3 |
| Carbon dioxide* | 1.75 | 4.9 | 6.0 | 6.4 |

*Expressed as carbon content related to the carbon content of the coal converted, % by weight The data of the table indicate that only a minor amount of carbon dioxide is formed in the process according to the invention. When comparing the data of Tests 1 and 4 it appears that if an aqueous liquid medium is applied, a relatively small amount of cooxidation partner is also sufficient to provide the desired results. From the comparison of the data of Tests 2 and 3 it follows that the amount of water-soluble products and the share of polycarboxylic acids in this latter fraction increase upon adding a catalyst with $Co^{2+}$ cation and $Br^-$ anion content to the mixture. The data of Test 4 indicate, in comparison to those of Test 3, that vanadium pentoxide catalyst particularly promotes the formation of polycarboxylic acids. As it appears from the data of Tests 2 to 4, the catalysts practically do not influence the conversion ratio of carbon, affecting the composition of the product mixture only.

What we claim is:

1. A method for the liquid phase oxidation of coal performed with oxygen, wherein the oxidation is performed solely in the presence of a non-aqueous cooxidation partner selected from the group of liquid hydrocarbons and oxygen-containing liquid hydrocarbons.

2. A method as claimed in claim 1, wherein liquid by-products or wastes of the hydrocarbon industry are applied as the non-aqueous cooxidation partner.

3. A method as claimed in claim 1 or 2, wherein 3 to 6 kg of the non-aqueous cooxidation partner are applied for 1 kg of coal.

4. A method as claimed in claim 1 wherein the oxidation is performed with air at 160°–240° C. under a pressure of 3–6 MPa.

5. A method as claimed in claim 1 wherein the non-aqueous cooxidation partner consists essentially of acetophenone.

* * * * *